(12) United States Patent
McMichael

(10) Patent No.: US 11,564,958 B2
(45) Date of Patent: Jan. 31, 2023

(54) COMPOSITIONS AND METHODS OF TREATMENT OF EHLERS-DANLOS SYNDROMES

(71) Applicant: RESOLYS BIO, INC., Delanson, NY (US)

(72) Inventor: John McMichael, Delanson, NY (US)

(73) Assignee: RESOLYS BIO, INC., Delanson, NY (US)

( * ) Notice: Subject to any disclaimer, the term of this patent is extended or adjusted under 35 U.S.C. 154(b) by 292 days.

(21) Appl. No.: 16/956,469

(22) PCT Filed: Dec. 21, 2018

(86) PCT No.: PCT/US2018/067271
§ 371 (c)(1),
(2) Date: Jun. 19, 2020

(87) PCT Pub. No.: WO2019/126737
PCT Pub. Date: Jun. 27, 2019

(65) Prior Publication Data
US 2020/0338147 A1    Oct. 29, 2020

Related U.S. Application Data

(60) Provisional application No. 62/608,687, filed on Dec. 21, 2017.

(51) Int. Cl.
| | | |
|---|---|---|
| *A61K 35/76* | (2015.01) | |
| *A61P 19/02* | (2006.01) | |
| *A61K 31/417* | (2006.01) | |
| *A61K 38/39* | (2006.01) | |
| *A61K 39/395* | (2006.01) | |

(52) U.S. Cl.
CPC ............ *A61K 35/76* (2013.01); *A61K 31/417* (2013.01); *A61K 38/39* (2013.01); *A61K 39/39541* (2013.01); *A61P 19/02* (2018.01)

(58) Field of Classification Search
CPC ........ A61K 31/417; A61K 35/76; A61P 19/02
See application file for complete search history.

(56) References Cited

U.S. PATENT DOCUMENTS

| | | | | |
|---|---|---|---|---|
| 4,704,273 | A * | 11/1987 | McMichael | A61K 39/395 424/212.1 |
| 2005/0261250 | A1 | 11/2005 | Daifotis et al. | |
| 2016/0185842 | A1 | 6/2016 | Marotta et al. | |

OTHER PUBLICATIONS

European Patent Application No. 18891544.1, Extended European Search Report, dated Jun. 21, 2021.

* cited by examiner

*Primary Examiner* — Kevin E Weddington
(74) *Attorney, Agent, or Firm* — Marshall, Gerstein & Borun LLP

(57) ABSTRACT

A method is provided for treatment of symptoms of Ehlers-Danlos Syndromes comprising administration of a composition comprising rubeola virus, histamine and collagen.

16 Claims, No Drawings

COMPOSITIONS AND METHODS OF TREATMENT OF EHLERS-DANLOS SYNDROMES

CROSS-REFERENCE TO RELATED APPLICATION

This application claims the benefit of priority to U.S. Provisional Patent Application No. 62/608,687, filed Dec. 21, 2017, the disclosure of which is incorporated herein by reference in its entirety.

BACKGROUND OF INVENTION

The present invention is directed to methods and compositions for treatment of Ehlers-Danlos Syndrome (EDS). EDS is a disease complex that includes more than a dozen genetic disorders that cause defective processing of collagen, and as a result, weakened connective tissues in the body. As a broad generalization, these disorders reduce the strength and increase the elasticity of connective tissues in the body's frame (particularly those holding joints together) and may create life threatening flaws or weaknesses in the structure and performance of organs such as kidneys, intestines and blood vessels. Symptoms may include loose joints, stretchy skin, and abnormal scar formation. These can be noticed at birth or in early childhood. Complications may include aortic dissection, joint dislocations, scoliosis, chronic pain, or early osteoarthritis.

EDS is due to a mutation in one of more than a dozen different genes and affects about 1 in 5,000 people globally. The prognosis depends on the specific type. While some types result in a normal life expectancy, those that affect blood vessels generally result in a shorter life expectancy. There is no known cure for EDS and treatment is supportive in nature. For example, physical therapy and bracing may help strengthen muscles and support joints.

The specific gene affected determines the type of EDS. Some cases result from a new mutation occurring during early development while others are inherited in an autosomal dominant or recessive manner. There are currently thirteen (13) different classifications of EDS. The two most common types are hypermobile EDS (hEDS) and classical EDS (cEDS). The remaining types are very rare.

EDS is estimated to affect 1 in 5,000 people. Hypermobile EDS currently known as hEDS, which includes but is not limited to what was previously designated Type 3 EDS, is the most common of the various syndromes, affecting from a third to half of the entire EDS population (1 in 10,000 to 15,000). Type 1 and 2—Classical EDS affects approximately 1 in 20,000 to 50,000 people. It is caused by autosomal dominant mechanism and affects type-V collagen, as well as type-I collagen. Type 1 Classical EDS typically presents with severe skin involvement while type 2 presents with mild to moderate skin involvement. Patients with the Classical Type EDS may experience the same symptoms as the Hypermobility Type (hEDS). The main difference between the hEDS and Classical Types is the Classical has more skin involvement while hEDS has more joint involvement, though patients with Classical EDS can also have severe joint issues and may respond well to MCC. Other variants such as vascular EDS (vEDS), which can lead to aortic dissection, represent even smaller patient populations. vEDS is the only variant with current treatments in development (celiprolol and irbesartin). The classical form of EDS was the subject of an earlier clinical study evaluating the efficacy of IGF-I, which improved tendon collagen synthesis rates. There remains a need for a drug for the treatment of hEDS.

Identification of the subtype of EDS helps identify the nature of pathologies and their causes. A diagnosis is important because, although EDS is not curable, many symptoms are treatable. Treatment is supportive in nature. In most cases pain is a principal patient complaint, typically accompanied by high fatigue due to muscles working overtime to keep the body together. Drugs are prescribed to treat the pain but do nothing for the underlying cause of disease. Non-pharmacologic treatment of EDS patients is limited to physical therapy to help muscles to work better with ligaments to support joints and keep them safe. Hydrotherapy is particularly helpful for aerobic exercise. Finally, bracing and casting can be helpful to support joints. Unfortunately, progressive disease often leads to a wheelchair and permanent incapacitation.

Hypermobile EDS (hEDS) which includes but is not limited to what was previously designated Type 3 EDS, is characterized primarily by joint hypermobility affecting both large and small joints, which may lead to recurrent joint dislocations and subluxations (partial dislocation). In general, people with this type have soft, smooth and velvety skin with easy bruising and chronic pain of the muscles and/or bones.

Classical EDS (cEDS) is associated with extremely elastic (stretchy), smooth skin that is fragile and bruises easily; wide, atrophic scars (flat or depressed scars); and joint hypermobility. Molluscoid pseudotumors (calcified hematomas over pressure points such as the elbow) and spheroids (fat-containing cysts on forearms and shins) are also frequently seen. Hypotonia and delayed motor development may occur.

Vascular EDS (vEDS) is characterized by thin, translucent skin that is extremely fragile and bruises easily. Arteries and certain organs such as the intestines and uterus are also fragile and prone to rupture. People with this type typically have short stature; thin scalp hair; and characteristic facial features including large eyes, a thin nose, and lobeless ears. Joint hypermobility is present, but generally confined to the small joints (fingers, toes). Other common features include club foot; tendon and/or muscle rupture; acrogeria (premature aging of the skin of the hands and feet); early onset varicose veins; pneumothorax (collapse of a lung); recession of the gums; and a decreased amount of fat under the skin.

Kyphoscoliosis EDS (kEDS) is associated with severe hypotonia at birth, delayed motor development, progressive scoliosis (present from birth), and scleral fragility. Affected people may also have easy bruising; fragile arteries that are prone to rupture; unusually small corneas; and osteopenia (low bone density). Other common features include a "marfanoid habitus" which is characterized by long, slender fingers (arachnodactyly); unusually long limbs; and a sunken chest (pectus excavatum) or protruding chest (pectus carinatum).

Arthrochalasia EDS (aEDS) is characterized by severe joint hypermobility and congenital hip dislocation. Other common features include fragile, elastic skin with easy bruising; hypotonia; kyphoscoliosis (kyphosis and scoliosis); and mild osteopenia.

Dermatosparaxis EDS (dEDS) is associated with extremely fragile skin leading to severe bruising and scarring; saggy, redundant skin, especially on the face; and hernias. Brittle Cornea Syndrome (BCS) characterized by thin cornea, early onset progressive keratoglobus; and blue sclerae.

Classical-like EDS (clEDS) is characterized by skin hyperextensibility with velvety skin texture and absence of atrophic scarring, generalized joint hypermobility (GJH) with or without recurrent dislocations (most often shoulder and ankle), and easily bruised skin or spontaneous ecchymoses (discolorations of the skin resulting from bleeding underneath).

Spondylodysplastic EDS (spEDS) is characterized by short stature (progressive in childhood), muscle hypotonia (ranging from severe congenital, to mild later-onset), and bowing of limbs.

Musculocontractural EDS (mcEDS) is characterized by congenital multiple contractures, characteristically adduction-flexion contractures and/or talipes equinovarus (clubfoot), characteristic craniofacial features, which are evident at birth or in early infancy, and skin features such as skin hyperextensibility, easy bruisability, skin fragility with atrophic scars, increased palmar wrinkling.

Myopathic EDS (mEDS) is characterized by congenital muscle hypotonia, and/or muscle atrophy, that improves with age, Proximal joint contractures (joints of the knee, hip and elbow); and hypermobility of distal joints (joints of the ankles, wrists, feet and hands).

Periodontal EDS (pEDS) is characterized by severe and intractable periodontitis of early onset (childhood or adolescence), lack of attached gingiva, pretibial plaques; and family history of a first-degree relative who meets clinical criteria.

Cardiac-valvular EDS (cvEDS) is characterized by severe progressive cardiac-valvular problems (aortic valve, mitral valve), skin problems (hyperextensibility, atrophic scars, thin skin, easy bruising) and joint hypermobility (generalized or restricted to small joints).

Hypermobile EDS (hEDS) (also known as Type III EDS) is the most common form of EDS but no genetic basis for its genesis has been identified. In general hEDS is considered less severe than the other types of EDS but significant complications, particularly those of the musculoskeletal system, do occur. The skin is often soft and can be mildly hyperextendible. Subluxations and dislocations which can be acutely painful are said to be common and can occur spontaneously or with minimal trauma. Degenerative joint disease, easy bruising and chronic pain are common with the syndrome.

Hypermobile, or loose, joints that are not held tightly together by normally functioning collagen undergo frequent subluxations, dislocations and pain. This can be a significant problem when hyperextensible joints move beyond their normal range. Early onset osteoarthritis is a common consequence of this joint hypermobility as well. Many patients with hypermobile joints also report fatigue, likely caused by muscles working overtime to keep the body together. EDS also presents with skin disorders such as hyperextensibility and tissue fragility. These characteristics, which can be noticed in early childhood, help define and differentiate between the multiple subtypes of EDS that are used for classification purposes.

Taken together all the fragmented data on pain manifestations and its possible underlying mechanisms in EDS indicate a complex pathogenesis. The slow progression from episodic, low-moderate, and treatment-responsive pain at single joints to chronic, severe and disabling pain affecting the entire body is indicative of multiple contributing pathologies. Some patients are able to localize pain and experience a satisfactory life, while others feel defeated and live a very restricted existence. For these reasons there remain a need in the art for more effective treatments of EDS and the symptoms of EDS.

Histamine [4-(2-aminoethyl)-imidazole or .beta.-imidazolyl-ethylamine] is a chemical substance possessing pronounced biological activities. It is a powerful stimulant of gastric secretion and constrictor of smooth muscle. It is a vasodilator and large doses cause a relatively rapid fall in blood pressure. It is frequently noted to be liberated by epithelial cells upon traumatic injury or stimulation by antigenic substances. Its storage in and release from mast cells and basophil granules and its role in Type I hypersensitivity reactions have been the subject of extensive study.

Of interest to the present application are the disclosures of U.S. Pat. No. 5,877,198 which is directed to the administration of histamine for the treatment of the symptoms of urinary incontinence and U.S. Pat. No. 6,156,780 which is directed to the administration of histamine for the treatment of the symptoms of fecal incontinence. Also of interest is the disclosure of published application US 2014/0121256 which is directed to the administration of histamine for the treatment of muscle weakness.

Of further interest to the present application is the disclosures of U.S. Pat. No. 4,521,405 which is directed to the administration of histamine and inactivated attenuated measles virus (rubeola) for the treatment of symptoms of Multiple Sclerosis and of U.S. Pat. No. 4,705,685 which is directed to the administration of histamine and inactivated attenuated measles virus (rubeola) for the treatment of chronic pain.

Also of interest to the present invention is the disclosure of U.S. Pat. No. 4,704,273 which is directed to a administering to a subject suffering from rheumatoid arthritis an effective amount of a composition comprising a mixture of histamine, immunoglobulin G provocative of rheumatoid factor formation or an immunologically active fraction thereof, collagen and attenuated measles virus (rubeola) for alleviating the symptoms of rheumatoid arthritis such as decreasing pain, increasing mobility and flexibility, decreasing swelling, decreasing inflammation and increasing energy. Other compositions comprising attenuated measles virus (rubeola) and histamine were reported to be useful in alleviating symptoms of rheumatoid arthritis while compositions comprising histamine alone or histamine in combination with immunoglobulin G provocative of rheumatoid factor formation were reported to not be useful in alleviating such symptoms.

The patent further discloses administration of compositions comprising histamine, measles virus (rubeola) vaccine and influenza virus vaccine; of histamine and measles virus vaccine; and of histamine and influenza virus vaccine. The patent reported that subjects receiving the combination of histamine and measles virus vaccine with and without influenza virus vaccine had improvement of symptoms which those treated with the combination of histamine and influenza virus vaccine did not. Subjects treated with collagen and immunoglobulin G provocative of rheumatoid factor formation without rubeola virus or histamine did not report improvement in symptoms.

BRIEF SUMMARY OF THE INVENTION

The present invention is directed to treatment of symptoms of Ehlers-Danlos Syndrome. In particular the invention is directed to treatment of one or more symptoms of Ehlers-Danlos Syndrome by the administration of a composition comprising rubeola virus, histamine and collagen and further optionally comprising immunoglobulin, including but not limited to IgG.

The invention is particularly directed to treatment of symptoms of hypermobile EDS (hEDS) and classical EDS (cEDS) and treatment of symptoms of EDS where the symptoms are selected from the group consisting of pain (including maladaptive pain without tissue damage) fatigue, range of motion, emesis, and general quality of life as measured by tools such as the Short Form Health Survey (SF36) for measuring quality of life (QOL) and other similar assessments.

The compositions of the invention comprise rubeola (measles) virus in a dosage of from 0.4 $TCID_{50}$ to 400 $TCID_{50}$, more preferably 1 $TCID_{50}$ to 10 $TCID_{50}$ and most preferably 4 $TCID_{50}$. Rubeola virus is commercially available in vaccine form such as attenuated live virus such as Attenuvax® (Merck & Co., Whitehouse Station, N.J.) but those of skill in the art would appreciate that other forms of rubeola virus including non-attenuated virus from other sources could be used in practice of the invention.

The composition further comprises histamine in a dosage of from 0.001 mg to 0.1 mg, more preferably 0.01 mg to 0.05 mg and most preferably 0.008 mg. Various forms of histamine can be used in the practice of the invention such as water soluble histamine salts including histamine phosphate. Those of skill in the art would appreciate other forms of histamine including histamine dihydrochloride would be useful in practice of the invention.

Collagen is present in the compositions of the invention in dosages of from 0.0001 mg to 0.1 mg, more preferably 0.001 mg to 0.01 mg and most preferably 0.002 mg. It is contemplated that any form of collagen from any source will be useful in practice of the invention and that the collagen may be denatured or non-denatured. Particularly preferred is bovine calf collagen such as is available from Sigma-Aldrich (also known as Millipore-Sigma).

According to one aspect of the invention immunoglobulin can be incorporated into the compositions comprising Rubeola virus, histamine and collagen. Such compositions can comprise Immunoglobulin in dosages of from 0.0001 mg to 0.3 mg, more preferably 0.001 mg to 0.03 mg and most preferably 0.003 mg. According to one aspect of the invention the Immunoglobulin is human serum derived immunoglobulin but the source and immunological specificity of the Immunoglobulin is not thought to be relevant to its utility in the practice of the invention.

A particularly preferred composition according to the invention comprises Rubeola virus at a dosage of 4 $TCID_{50}$ (Attenuvax®, Merck & Co., Whitehouse Station, N.J.), 0.008 mg histamine (Hollister Stier Allergy, Spokane, Wash.), and 0.002 mg calf or bovine derived collagen from Sigma-Aldrich (also known as Millipore-Sigma) in a phenylated saline buffer.

The compositions of the invention can be combined with pharmaceutically acceptable diluents, adjuvants and carriers as would be known to the art. The compositions can also be administered to the subjects to be treated parenterally or enterally. According to one aspect of the invention the compositions can be administered parenterally to the subjects to be treated such as by subcutaneous injection but other sublingual administration is particularly preferred.

DETAILED DESCRIPTION OF THE INVENTION

The present invention is directed to treatment of symptoms of Ehlers-Danlos Syndrome. In particular the invention is directed to treatment of symptoms of one or more symptoms of Ehlers-Danlos Syndrome by the administration of compositions comprising an effective amount of a composition comprising rubeola virus, histamine and collagen, According to one aspect of the invention a composition is provided which comprises a composition comprising rubeola virus, histamine and collagen. The components can be solubilized in phenylated saline and formulated to be administered by drop (0.05 mL) sublingually at various intervals daily to treat symptoms of EDS and particularly hEDS. Nevertheless, given the heterogeneous causes of the many syndromes that fall under the Ehlers-Danlos label it is anticipated that many patients suffering from other types of EDS will respond to treatment with the compositions of the invention.

According to one aspect of the invention EDS symptoms of pain, fatigue, emesis can be reduced and joint mobility (range of motion) and quality of life measures can be improved by administration of the compositions of the invention.

The compositions of the invention comprise rubeola (measles) virus in a dosage of from 0.4 $TCID_{50}$ to 400 $TCID_{50}$, more preferably 1 $TCID_{50}$ to 10 $TCID_{50}$ and most preferably 4 $TCID_{50}$. Rubeola virus is commercially available in vaccine form such as attenuated live virus such as Attenuvax® (Merck & Co., Whitehouse Station, N.J.) but those of skill in the art would appreciate that other forms of rubeola virus from other sources could be used in practice of the invention.

The composition further comprises histamine in a dosage of from 0.001 mg to 0.1 mg, more preferably 0.01 mg to 0.05 mg and most preferably 0.008 mg. Various forms of histamine can be used in the practice of the invention such as water soluble histamine salts including histamine dihydrochloride and histamine phosphate. One particularly useful source of histamine is Hollister-Stier Allergy (Spokane Wash.) Those of skill in the art would appreciate that other forms of histamine would be useful in practice of the invention.

Collagen is present in the compositions of the invention in dosages of from 0.0001 mg to 0.1 mg, more preferably 0.001 mg to 0.01 mg and most preferably 0.002 mg. Useful collagen can be denatured or undenatured and of any type derived from any animal source but a particularly preferred collagen is calf or bovine derived collagen from Sigma-Aldrich (also known as Millipore-Sigma).

According to one aspect of the invention immunoglobulin can be incorporated into the compositions comprising Rubeola virus, histamine and collagen. Such compositions can comprise Immunoglobulin in dosages of from 0.0001 mg to 0.3 mg, more preferably 0.001 mg to 0.03 mg and most preferably 0.003 mg. According to one aspect of the invention the immunoglobulin is human immune globulin such as is commercially available as GamaSTAN™ (Talecris Biotherapeutics, Inc. Research Triangle Park, N.C.) which is believed to be primarily IgG but the immunological specificity of the Immunoglobulin is not thought to be relevant to its utility in the practice of the invention.

A particularly preferred composition according to the invention comprises Rubeola virus at a dosage of 4 $TCID_{50}$ (Attenuvax®, Merck & Co., Whitehouse Station, N.J.), 0.008 mg histamine (Hollister Stier Allergy, Spokane, Wash.), 0.002 mg calf or bovine derived collagen from Sigma-Aldrich (also known as Millipore-Sigma) and 0.003 mg Immunoglobulin (GamaSTAN™ Talecris Biotherapeutics, Inc. Research Triangle Park, N.C.) in a phenylated saline buffer.

It is preferred that initial treatment will involve four doses per day but patients can titrate their therapy to fewer doses after experiencing a therapeutic effect.

The compositions of the invention can be combined with pharmaceutically acceptable diluents, adjuvants and carriers as would be known to the art. It is contemplated that other suitable components could be combined with the components of the invention but none are required. The compositions can also be administered to the subjects to be treated parenterally or enterally. According to one aspect of the invention the compositions can be administered parenterally to the subjects to be treated such as by subcutaneous injection but other sublingual administration is particularly preferred.

Example 1

According to this example, a woman diagnosed with hEDS was treated by sublingual administration four times daily with one drop (0.05 ml) of a composition comprising Rubeola virus at a dosage of 4 $TCID_{50}$ (Attenuvax®, Merck & Co., Whitehouse Station, N.J.), 0.008 mg histamine (Hollister Stier Allergy, Spokane, Wash.), 0.002 mg bovine derived collagen from Sigma-Aldrich (also known as Millipore-Sigma) and 0.003 mg Immunoglobulin (GamaSTAN™ Talecris Biotherapeutics, Inc. Research Triangle Park, N.C.) in a phenylated saline buffer.

When the subject was evaluated after ten (10) days of treatment her physician reported the following:

"After only 10 days, she has had a remarkable alteration of her symptomology. Previously, she was a stay-at-home mother with a fulltime nanny, unable to care for her 3 children, couch-bound & only able to leave the house for perhaps an hour per day, only shop 1x/week after which she would be unfunctional due to fatigue & brain fog. She was consuming both LongActing Oxycontin and Oxycodone/Tylenol @ 6/day."

"Currently she has 'more energy than in past 10 years', is 'chasing the kids' around the house, was out of the house for 6 hours yesterday with no collapse afterwards. Her pain has diminished to point of reducing her pain meds from 6 Percocet/day to 2/d within a week, without any withdrawal symptoms. (She has been at this level of daily narcotics for 2 years)."

Example 2

According to this example, a different female subject diagnosed with Type 3 Ehlers-Danlos Syndrome who had been suffering from the syndrome for about eight (8) years was treated by sublingual administration four times daily of one drop (0.05 ml) of a composition comprising Rubeola virus at a dosage of 4 $TCID_{50}$ (Attenuvax®, Merck & Co., Whitehouse Station, N.J.), 0.008 mg histamine (Hollister Stier Allergy, Spokane, Wash.), 0.002 mg bovine derived collagen from Sigma-Aldrich (also known as Millipore-Sigma) and 0.003 mg Immunoglobulin (GamaSTAN™ Talecris Biotherapeutics, Inc. Research Triangle Park, N.C.) in a phenylated saline buffer.

When the subject was evaluated after approximately 60 days of days of treatment the treating physician reported the following:

"Patient reported that she had decreased her pain medication from where it was when we started. Her Fentanyl patch has decreased from 125 to 37 mg and the Gabapentin has decreased from 1200 to 300 to 600 at night. Her energy level was evidenced to be increased as the patient sponta-neously lifted herself out of her wheelchair into a chair in our office. This observation of increased energy was reinforced by a report from her mother indicating that she was doing more for herself at home. Patient still reported spontaneously dislocating, and her sleep intervals have not apparently increased. Her personality was improved since last visit and she was more civil in her responses and her interactions."

Example 3

According to this example, a middle aged male subject diagnosed with Type 3 Ehlers-Danlos Syndrome who had been suffering from the syndrome was treated by was treated by sublingual administration of one drop (0.05 ml) of a composition comprising Rubeola virus at a dosage of 4 $TCID_{50}$ (Attenuvax®, Merck & Co., Whitehouse Station, N.J.), 0.008 mg histamine (Hollister Stier Allergy, Spokane, Wash.), 0.002 mg bovine derived collagen from Sigma-Aldrich (also known as Millipore-Sigma) and 0.003 mg Immunoglobulin (GamaSTAN™ Talecris Biotherapeutics, Inc. Research Triangle Park, N.C.) in a phenylated saline buffer. The subject reported reduced pain, reduced fatigue and improved quality of life.

Example 4

According to this example a 61 year old female with joint hypermobility since childhood was treated She has not been classified as to EDS type by genetic evaluation, but would be classified as suffering from hEDS in the present vernacular. She is the owner of a small deli store where she works six days per week. At the time of initiating therapy she complained of soreness, tiredness, joint aches and pains, and difficulty making it through her long work days.

The subject was treated by sublingual administration four times daily of one drop (0.05 ml) of a three component composition comprising 4 $TCID_{50}$ (Attenuvax®, Merck & Co., Whitehouse Station, N.J.), 0.008 mg histamine (Hollister Stier Allergy, Spokane, and WA), 0.002 mg bovine derived collagen from Sigma-Aldrich (also known as Millipore-Sigma) in a phenylated saline buffer.

After six weeks of treatment with the three component composition the subject was treated by sublingual administration four times daily of one drop (0.05 ml) of administration of a four component composition comprising Rubeola virus at a dosage of 4 $TCID_{50}$ (Attenuvax®, Merck & Co., Whitehouse Station, N.J.), 0.008 mg histamine (Hollister Stier Allergy, Spokane, Wash.), 0.002 mg calf or bovine derived collagen from Sigma-Aldrich (also known as Millipore-Sigma) and 0.003 mg Immunoglobulin (GamaSTAN™ Talecris Biotherapeutics, Inc. Research Triangle Park, N.C.) in a phenylated saline buffer.

The subject noted that while all the previous symptoms were still present were significantly reduced. Although she did not mention much about the state of loose joints at the first visit, at the six week mark she did say her shoulders felt better, or tighter. The subject reported reduced fatigue during the day after 10-14 days of treatment and reported that reduced pain was evident before the two week mark. No adverse effects were reported.

Example 5

A 27 year old male diagnosed with hEDS (Type 3 EDS) suffered from weakness, pain, and joint dislocations and had difficulty sleeping and reported suffering from "brain fog."

The subject also reported that the symptoms of his condition made it difficult for him to maintain employment.

The subject was treated by sublingual administration four times daily of one drop (0.05 ml) of a three component composition comprising Rubeola virus at a dosage of 4 $TCID_{50}$ (Attenuvax®, Merck & Co., Whitehouse Station, N.J.), 0.008 mg histamine (Hollister Stier Allergy, Spokane, Wash.), and 0.002 mg bovine derived collagen from Sigma-Aldrich (also known as Millipore-Sigma) in a phenylated saline buffer.

After six weeks of treatment the subject reported that he felt stronger, had considerably less joint pain, had better sleeping patterns and reduced "brain fog." He especially noted that he could rotate his arm at the shoulder for the first time in months without pain and with an increase in range of motion without dislocation. No adverse effects were reported.

After six weeks of treatment with the three component composition the subject was treated by sublingual administration four times daily of one drop (0.05 ml) of administration of a four component composition comprising dosage of 4 $TCID_{50}$ (Attenuvax®, Merck & Co., Whitehouse Station, N.J.), 0.008 mg histamine (Hollister Stier Allergy, Spokane, Wash.), 0.002 mg bovine derived collagen from Sigma-Aldrich (also known as Millipore-Sigma) and 0.003 mg Immunoglobulin (GamaSTAN™ Talecris Biotherapeutics, Inc. Research Triangle Park, N.C.) in a phenylated saline buffer. Administration of the four component mixture further comprising Immunoglobulin maintained the improved symptoms but did not significantly improve them compared to when they were treated with the three component mixture.

Ten additional patients suffering from forms of EDS have been treated by administration of the compositions of the invention and those subjects have reported improvements in symptoms similar to those reported above.

Example 6

According to this example, a 21 year old female subject presented with a high arched palate, joint hypermobility, joint pain/dislocations, abnormal skin with easy bruising, abnormal scars, delayed wound healing, skin stretching and striae and myopia was diagnosed with hEDS and had a Brighton score of 6/9. She also had soft/velvety skin, easy bruising, symptoms of Postural orthostatic tachycardia syndrome (POTS), and muscle pain.

She was treated by sublingual administration four times daily of one drop (0.05 ml) of a three component composition comprising Rubeola virus at a dosage of 4 $TCID_{50}$ (Attenuvax®, Merck & Co., Whitehouse Station, N.J.), 0.008 mg histamine (Hollister Stier Allergy, Spokane, Wash.), and 0.002 mg bovine derived collagen from Sigma-Aldrich (also known as Millipore-Sigma) in a phenylated saline buffer.

The results of treatment presented in Table 1 below show improved generalized pain and improvements in the knee function. There were no changes in hypermobility, soft/velvety skin, or easy bruising but she was able to exercise for longer periods without pain and was eating a healthier diet. On one case, where she missed her dosage she passed out as a result of POTS.

TABLE 1

SF-36 scores: initiation of therapy and most current (0 = poor; 100 = optimal)

| | Day 1 | Day 471 | Difference |
|---|---|---|---|
| physical functioning | 40 | 80 | 40 |
| role limitations due physical health | 0 | 50 | 50 |
| role limitations due emotional problems | 33.3 | 0 | −33.3 |
| energy/fatigue | 15 | 15 | 0 |
| emotional well-being | 36 | 12 | −24 |
| social functioning | 37.5 | 25 | −12.5 |
| pain | 12.5 | 57.5 | 45 |
| general health | 10 | 55 | 45 |

Example 7

According to this example, a 17 year old female subject presented with Initial symptoms of knee and shoulder dislocations, chronic fatigue and illnesses (e.g. mononucleosis, strep throat), easy scarring and bruising, swollen glands, and memory fog. She also had a 8/9 Brighton score and a physical exam revealed chronic fatigue, general pain, purplish, velvety skin highly reactive to hot/cold. The subject also presented as being uncomfortable, and having emotional difficulties including crying, panic attacks, and depression, shaking hands, pain and tingling throughout body, joint dislocations, irritable bowel syndrome, acid reflux, nausea, fatigue, dizziness, difficulty swallowing, rashes, dry-eye syndrome and mouth ulcerations.

She was treated by sublingual administration four times daily of one drop (0.05 ml) of a three component composition comprising Rubeola virus at a dosage of 4 $TCID_{50}$ (Attenuvax®, Merck & Co., Whitehouse Station, N.J.), 0.008 mg histamine (Hollister Stier Allergy, Spokane, Wash.), and 0.002 mg bovine derived collagen from Sigma-Aldrich (also known as Millipore-Sigma) in a phenylated saline buffer.

After two weeks of treatment the patent reported improvement in all areas saying she had more energy and reported feeling as though she has normal health and has participated in more aspects of normal living including work, socializing and exercise. The results of treatment are presented in Table 2 below.

TABLE 2

SF-36 scores: initiation of therapy and most current (0 = poor: 100 = optimal)

| | Day 1 | Day 241 | Difference |
|---|---|---|---|
| physical functioning | 50 | 75 | 25 |
| role limitations due physical health | 50 | 50 | 0 |
| role limitations due emotional problems | 67 | 100 | 33 |
| energy/fatigue | 15 | 40 | 25 |
| emotional well-being | 60 | 64 | 4 |
| social functioning | 50 | 62.5 | 12.5 |
| pain | 45 | 55 | 10 |
| general health | 20 | 35 | 15 |

Example 8

According to this example, subjects diagnosed with hEDS, cEDS and other EDS variants are divided into control and treatment groups with the treatment groups treated according to a protocol in which they were treated by sublingual administration four times daily of one drop (0.05 ml) of a three component composition comprising Rubeola virus at a dosage of 4 $TCID_{50}$ (Attenuvax®, Merck & Co., Whitehouse Station, N.J.), 0.008 mg histamine (Hollister Stier Allergy, Spokane, Wash.), and 0.002 mg calf or bovine derived collagen from Sigma-Aldrich (also known as Millipore-Sigma) in a phenylated saline buffer.

The control and test subjects are evaluated prior to treatment for pain, fatigue, range of motion, emesis, and general quality of life such as can be measured by tools such as the Short Form Health Survey (SF36) and then periodically over a 90 day trial period and at the end of the trial period to determine the degree to which each symptom is improved.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed:

1. A method of treating symptoms of an Ehlers-Danlos Syndrome in a subject suffering therefrom comprising the step of administering to said subject an effective amount of a composition comprising rubeola virus, histamine and collagen wherein the symptom is selected from the group consisting of fatigue, range of motion and emesis.

2. The method of claim 1 wherein the Ehlers-Danlos Syndrome is selected from the group of hypermobile EDS (hEDS) and classical EDS (cEDS).

3. The method of claim 1 wherein the Ehlers-Danlos Syndrome is hypermobile EDS (hEDS).

4. The method of claim 1 wherein the composition comprises rubeola virus in a dosage of from 0.4 $TCID_{50}$ to 400 $TCID_{50}$.

5. The method of claim 1 wherein the composition comprises histamine in a dosage of from 0.001 mg to 0.1 mg.

6. The method of claim 1 wherein the histamine is a water soluble histamine salt.

7. The method of claim 1 wherein the histamine is histamine phosphate.

8. The method of claim 1 wherein the composition comprises collagen in a dosage of from 0.0001 mg to 0.1 mg.

9. The method of claim 1 wherein the composition further comprises Immunoglobulin.

10. The method of claim 9 wherein the composition comprises Immunoglobulin in a dosage of from 0.0001 mg to 0.3 mg.

11. The method of claim 9 in which the immunoglobulin is human immunoglobulin.

12. The method of claim 9 in which the immunoglobulin is IgG.

13. The method of claim 4 in which the composition comprises rubeola virus in a dosage of from 1 $TCID_{50}$ to 10 $TCID_{50}$.

14. The method of claim 5 in which the composition comprises histamine in a dosage of from 0.01 mg to 0.05 mg.

15. The method of claim 8 in which the composition comprises collagen in a dosage of from 0.001 mg to 0.01 mg.

16. The method of claim 10 in which the composition comprises immunoglobulin in a dosage of from 0.001 mg to 0.03 mg.

* * * * *